United States Patent
Potocek et al.

(10) Patent No.: US 10,115,561 B2
(45) Date of Patent: Oct. 30, 2018

(54) METHOD OF ANALYZING SURFACE MODIFICATION OF A SPECIMEN IN A CHARGED-PARTICLE MICROSCOPE

(71) Applicant: FEI Company, Hillsboro, OR (US)

(72) Inventors: Pavel Potocek, Eindhoven (NL); Faysal Boughorbel, Eindhoven (NL); Mathijs Petrus Wilhelmus van den Boogaard, Boxtel (NL); Emine Korkmaz, Veldhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 15/177,242

(22) Filed: Jun. 8, 2016

(65) Prior Publication Data

US 2016/0365224 A1 Dec. 15, 2016

(30) Foreign Application Priority Data

Jun. 9, 2015 (EP) ..................... 15171227

(51) Int. Cl.
| | | |
|---|---|---|
| *H01J 37/30* | (2006.01) | |
| *G01N 1/28* | (2006.01) | |
| *H01J 37/304* | (2006.01) | |
| *H01J 37/20* | (2006.01) | |
| *H01J 37/244* | (2006.01) | |
| *H01J 37/26* | (2006.01) | |

(Continued)

(52) U.S. Cl.
CPC .......... *H01J 37/3005* (2013.01); *G01N 1/286* (2013.01); *H01J 37/20* (2013.01); *H01J 37/244* (2013.01); *H01J 37/26* (2013.01); *H01J 37/317* (2013.01); *H01J 37/304* (2013.01); *H01J 37/3056* (2013.01); *H01J 2237/221* (2013.01)

(58) Field of Classification Search
None
See application file for complete search history.

(56) References Cited

U.S. PATENT DOCUMENTS

| | | |
|---|---|---|
| 6,175,417 B1 | 1/2001 | Do et al. |
| 6,399,944 B1 | 6/2002 | Vasilyev et al. |
| (Continued) | | |

FOREIGN PATENT DOCUMENTS

| | | |
|---|---|---|
| EP | 2824445 A1 | 1/2015 |
| EP | 2869328 A1 | 5/2015 |

OTHER PUBLICATIONS

A.A. Goshtasby, "Similarity and Dissimilarity Measures", Image Registration, (Springer, 2012).*

(Continued)

*Primary Examiner* — David E Smith
*Assistant Examiner* — James Choi
(74) *Attorney, Agent, or Firm* — Scheinbeg & Associates, P.C.; Michael O. Scheinberg

(57) ABSTRACT

A method of investigating a specimen using a charged particle microscope, including:
   Producing and storing a first image, of a first, initial surface of the specimen;
   In a primary modification step, modifying said first surface, thereby yielding a second, modified surface;
   Producing and storing a second image, of said second surface;
   Using a mathematical Image Similarity Metric to perform pixel-wise comparison of said second and first images, so as to generate a primary figure of merit for said primary modification step.

20 Claims, 5 Drawing Sheets

(51) Int. Cl.
*H01J 37/317* (2006.01)
*H01J 37/305* (2006.01)

(56) References Cited

U.S. PATENT DOCUMENTS

| | | | |
|---|---|---|---|
| 8,232,523 B2 | 7/2012 | Boughorbel et al. | |
| 2001/0027917 A1 | 10/2001 | Ferranti et al. | |
| 2002/0092985 A1* | 7/2002 | Ishitani | G01N 23/04 250/309 |
| 2003/0047691 A1 | 3/2003 | Musil et al. | |
| 2004/0121069 A1 | 6/2004 | Ferranti et al. | |
| 2006/0219953 A1 | 10/2006 | Carleson | |
| 2006/0228634 A1 | 10/2006 | Bret et al. | |
| 2007/0114407 A1 | 5/2007 | Schamber et al. | |
| 2010/0116977 A1 | 5/2010 | Young et al. | |
| 2011/0115129 A1 | 5/2011 | Straw et al. | |
| 2011/0248164 A1 | 10/2011 | Straw et al. | |
| 2015/0048815 A1* | 2/2015 | Barends | H01J 37/20 324/149 |
| 2015/0136977 A1* | 5/2015 | Buxbaum | G01N 1/32 250/307 |
| 2016/0013015 A1 | 1/2016 | Potocek et al. | |

OTHER PUBLICATIONS

Akselrod-Ballin, Ayelet et al., "Accelerating Image Registration With the Johnson Lindenstrauss Lemma: Application to Imaging 3-0 Neural Ultrastructure With Electron Microscopy," IEEE Transaction on Medical Imaging, IEEE Service Center, Piscataway, N.J. U.S., vol. 30, No. 7, Jul. 1, 2011, pp. 1427-1438.
Goshtasby, Ardeshir A., "Chapter 2: Similarity and Dissimilarity Measures," Advances in Computer Vision Pattern Recognition: Image Registration, Nov. 1, 2012, Springer, London, vol. 23, pp. 7-66.
http://en.wikpedia.org/wiki/Electron_microscope.
http://en.wikipedia.org/wiki/Scanning_electron_microscope.
http://en.wikipedia.org/wiki/Transmission_electron_microscopy.
http://en.wikipedia.org/wiki/Scanning_transmission_electron_microscopy.
http://en.wikipedia.org/wiki/Scanning_Helium_Ion_Microscope.
http://www.innovationmagazine.com/innovation/volumes/v7n1/coverstory3.shtml.
http://cbs.fas.harvard.edu/science/connectome-project/atium.
Escovitz, W.H. "Scanning Transmission Ion Microscope with a Field Ion Source," Proc. Nat. Acad. Sci. USA 72(5), pp. 1826-1828 (1975).

* cited by examiner

148

183

I 79 (---)

I 80 (---)

Δ I 80 – I 79 (---)

I 63

I 64

Δ I 64 – I 63

METHOD OF ANALYZING SURFACE MODIFICATION OF A SPECIMEN IN A CHARGED-PARTICLE MICROSCOPE

The invention relates to a method of investigating a specimen using:
A charged-particle microscope comprising:
  A specimen holder, for holding the specimen;
  A source, for producing a beam of charged-particle radiation;
  An illuminator, for directing said beam so as to irradiate a surface of the specimen;
  An imaging detector, for receiving a flux of radiation emanating from the specimen in response to said irradiation, so as to produce an image of at least part of said surface;
  An apparatus that can be invoked to modify said surface by performing thereon a process chosen from the group comprising material removal, material deposition, and combinations hereof.

The invention also relates to a charged-particle microscope that can be used in performing such a method.

Charged-particle microscopy is a well-known and increasingly important technique for imaging microscopic objects, particularly in the form of electron microscopy. Historically, the basic genus of electron microscope has undergone evolution into a number of well-known microscope species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. More specifically:
  In a SEM, irradiation of a specimen by a scanning electron beam precipitates emanation of "auxiliary" radiation from the specimen, in the form of secondary electrons, backscattered electrons, X-rays and photoluminescence (infrared, visible and/or ultraviolet photons), for example; one or more components of this emanating radiation is/are then detected and used for image accumulation purposes, and/or spectroscopic analysis (as in the case of EDX (Energy-Dispersive X-Ray Spectroscopy), for example).
  In a TEM, the electron beam used to irradiate the specimen is chosen to be of a high-enough energy to penetrate the specimen (which, to this end, will generally be thinner than in the case of a SEM specimen); the flux of transmitted electrons emanating from the specimen can then be used to create an image, or produce a spectrum (as in the case of EELS, for example; EELS=Electron Energy-Loss Spectroscopy). If such a TEM is operated in scanning mode (thus becoming a STEM), the image/spectrum in question will be accumulated during a scanning motion of the irradiating electron beam.

More information on some of the topics elucidated here can, for example, be gleaned from the following Wikipedia links:
  en.wikipedia.org/wiki/Electron_microscope
  en.wikipedia.org/wiki/Scanning_electron_microscope
  en.wikipedia.org/wiki/Transmission_electron_microscopy
  en.wikipedia.org/wiki/Scanning_transmission_electron_microscopy As an alternative to the use of electrons as irradiating beam, charged-particle microscopy can also be performed using other species of charged particle. In this respect, the phrase "charged particle" should be broadly interpreted as encompassing electrons, positive ions (e.g. Ga or He ions), negative ions, protons and positrons, for instance. As regards ion-based microscopy, some further information can, for example, be gleaned from sources such as the following:
  en.wikipedia.org/wiki/Scanning_Helium_Ion_Microscope
  W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975).
  www.innovationmagazine.com/innovation/volumes/v7n1/coverstory3.shtml It should be noted that, in addition to imaging and/or spectroscopy, a charged-particle microscope (CPM) may also have other functionalities, such as examining diffractograms, performing (localized) surface modification (e.g. milling, etching, deposition), etc.

In all cases, a Charged-Particle Microscope (CPM) will comprise at least the following components:
  A radiation source, such as a Schottky electron source or ion gun.
  An illuminator, which serves to manipulate a "raw" radiation beam from the source and perform upon it certain operations such as focusing, aberration mitigation, cropping (with a stop/iris/condensing aperture), filtering, etc. It will generally comprise one or more charged-particle lenses, and may comprise other types of particle-optical component also. If desired, the illuminator can be provided with a deflector system that can be invoked to cause its output beam to perform a scanning motion across the specimen being investigated.
  A specimen holder, on which a specimen under investigation can be held and positioned (e.g. tilted, rotated). If desired, this holder can be moved so as to effect a scanning motion of the beam w.r.t. the specimen. In general, such a specimen holder will be connected to a positioning system such as a mechanical stage.
  A detector, which may be unitary or compound/distributed in nature, and which can take many different forms, depending on the radiation/entity being recorded. Such a detector may, for example, be used to register an intensity value, to capture an image, or to record a spectrum. Examples include photomultipliers (including solid-state photomultipliers, SSPMs), photodiodes, (pixelated) CMOS detectors, (pixelated) CCD detectors, photovoltaic cells, etc., which may, for example, be used in conjunction with a scintillator film, for instance. For X-ray detection, use is typically made of a so-called Silicon Drift Detector (SDD), or a Silicon Lithium (Si(Li)) detector, for example. Typically, a CPM will comprise several detectors, of various types.

In the case of a transmission-type CPM (such as a (S)TEM), use will also be made of:
  An imaging system, which essentially takes charged particles that are transmitted through a specimen (plane) and directs (focuses) them onto analysis/sensing equipment, such as a detection/imaging device, spectroscopic unit, etc. As with the illuminator referred to above, the imaging system may also perform other functions, such as aberration mitigation, cropping, filtering, etc., and it will generally comprise one or more charged-particle lenses and/or other types of particle-optical components.

In what follows, the invention may—by way of example—sometimes be set forth in the specific context of electron microscopy. However, such simplification is intended solely for clarity/illustrative purposes, and should not be interpreted as limiting.

There are many instances of methods as set forth in the opening paragraph above, in which surface modification is performed with the aid of an apparatus/module that can be located ex situ (outside the CPM) or in situ (within the CPM). Examples of such surface modification include the following:

(i) A mechanical cutting tool (subtractive/material removal process):
Here, a contact tool such as a microtome, diamond scoring tool, obsidian blade, mill or lathe is used (in one or more runs) to cut/shave/pear a slice of material from (part of) the specimen surface.

(ii) Focused Particle Beam milling (subtractive/material removal process):
Here, a focused particle beam (e.g. an ion or electron beam) of a chosen energy/size can be scanned across (part of) the specimen surface so as to ablate material therefrom. If desired, this procedure can be repeated in successive iterations, so as to remove successively greater thicknesses of material. The procedure lends itself to patterned material removal, if desired.

(iii) Etching apparatus (subtractive/material removal process):
In this case, a chemical reagent (such as gas-phase etchant) is used to remove material from the specimen surface. If desired, this process can be activated/catalyzed using a focused particle beam, which allows the process to be made highly localized/patterned, if required. Examples of such an approach include IBIE (Ion-Beam-Induced Etching) and EBIE (Electron-Beam-Induced Etching).

(iv) Beam-Induced Deposition (additive/material deposition process):
Examples here include IBID (Ion-Beam-Induced Deposition) and EBID (Electron-Beam-Induced Deposition), in which a focused beam is used to (locally) instigate/precipitate deposition of material from a cloud of precursor gas.

(v) Physical Vapor Deposition (PVD) (additive/material deposition process):
Examples include sputtering and Molecular Beam Epitaxy (MBE), for instance.

(vi) Chemical Vapor Deposition (CVD) (additive/material deposition process):
Specific examples include PCVD (Plasma-assisted CVD) and MOCVD (Metal-Organic CVD), for instance.

Techniques (i)-(iv) can (but don't necessarily have to) be performed using in situ modules in CPMs; technique (i), for example, can also be performed ex situ, as in the case of the so-called ATLUM tool (Automated Tape-collecting Lathe UltraMicrotome), as set forth, for example, in the following link:
cbs.fas.harvard.edu/science/connectome-project/atlum
Techniques (v) and (vi) are conventionally performed ex situ, but, in principle, could also be performed using an in situ module.

Specific ways in which to employ surface modification techniques in CPMs are, for example, set forth in the following documents:
U.S. Pat. No. 8,232,523, in which physical slicing (e.g. with a microtome) is combined with computational image reconstruction so as to increase the depth range of the reconstruction;

EP 2824445 A1, in which various surface modification techniques are used to improve the Raman spectroscopy signal from a region of interest on a specimen.

A problem with such methods is that, since the CPM in which the surface-modified specimen is imaged will typically have nanometer or sub-nanometer resolution, and since the specimen in question will often be very delicate/brittle (e.g. because it is extremely thin (as in the case of a TEM specimen) or because it has been vitrified, for instance), the employed surface modification technique will have to be performed very accurately if it is to produce satisfactory results (e.g. qualitatively, quantitatively, and in terms of yield/throughput in the context of possible re-runs, touch-ups, sample damage, etc.). To date, there is no accurate way of monitoring such operations: instead, they tend to be rather hit-and-miss and haphazard in nature, and to rely heavily on previous experience/skill of the person performing the specimen investigation, and also to a certain extent on luck.

It is an object of the invention to address these issues. More specifically, it is an object of the invention to provide a way in which surface modification techniques as referred to above can be monitored. In particular, it is an object of the invention that such monitoring should enable relatively fast identification of a failed or corrupted surface modification attempt. In addition, it is an object of the invention to provide a monitoring technique that can potentially produce both qualitative and quantitative output.

These and other objects are achieved in a method as set forth in the opening paragraph above, which method is characterized by the following steps:
Producing and storing a first image, of a first, initial surface of the specimen;
In a primary modification step, invoking said apparatus so as to modify said first surface, thereby yielding a second, modified surface;
Producing and storing a second image, of said second surface;
Using a mathematical Image Similarity Metric (ISM) to perform pixel-wise comparison of said second and first (CPM) images, so as to generate a primary Figure Of Merit (FOM) for said primary modification step.

The current invention makes use of the fact that, after surface-modification, the specimen is transferred to a device (CPM) with imaging capability. It also makes use of the fact that a mathematical ISM can be used as a basis to perform automatic pixel-wise comparison of images using several objectively definable criteria, on the basis of which one can generate a FOM or "score" (e.g. based on a degree of correlation) that is a quantifier of the similarity (or dissimilarity) of the images in question; in so doing, the ISM treats (and preserves) the images as mathematical fields that are compared in a coordinate-by-coordinate (pixel-by-pixel) manner, thereby allowing (inter-image/intra-image) shape change detection and quantification that would not be possible if one were to perform a field-destroying (scalarizing) operation on the images, such as summing or integration, for example. Consequently, when such an ISM is performed on "before" and "after" images (abovementioned first and second images, respectively) pertaining to a given surface modification attempt, it can be used to (autonomously) determine what effect (if any) said attempt had on the surface in question. For example:

(a) If a FOM arising from comparison of said "before" and "after" images has a value above a pre-defined upper threshold, then one can adjudge that the surface modification attempt in question has failed/missed (e.g. because of poor alignment/calibration, process failure (such as a blocked gas conduit, beam misfire, etc.), failed synchronization, etc.). Considering a specific instance in which the employed ISM is the so-called Structural Similarity Index Metric (SSIM), then an upper-limit FOM-value (e.g. at or very near +1) could be interpreted in this way.

(b) Conversely, if a FOM arising from comparison of said "before" and "after" images is below a pre-defined lower threshold, then one can adjudge that the surface modification attempt in question has corrupted the surface in some way, e.g. by leaving debris thereon, or causing unintended mechanical damage thereto. Again considering the specific instance of the abovementioned SSIM, a lower-limit FOM-value (e.g. at or very near −1 or 0, depending on the employed SSIM definition/normalization) could be interpreted in this way.

(c) Between these two extremes, one can define an ideal "FOM band" corresponding to optimal performance of the surface modification technique. If the FOM lies outside this band (but within the lower and upper threshold values referred to above), then one can conclude that the surface modification attempt has been partially successful, but sub-optimal.

In situations (a) and (c), one could, for example, consider trying another surface modification attempt with adjusted parameters (such as cutting tool/beam position, assistive gas pressure, duration of procedure, etc.); if required, this could be done in successive iterations, ultimately converging toward a goal FOM value. In situation (b), one could consider cleaning/reconditioning the specimen surface before proceeding with further activities; if required, this process could also be done in successive steps/iterations, ultimately converging toward a goal FOM value. From these examples, it is seen that the invention provides a useful monitor on a procedure that is otherwise notoriously obscure.

As regards the actual ISM used in the present invention, there are various possibilities. One of these—the SSIM—has already been alluded to above, and produces a FOM value $F_{SSIM}(A, B)$ for the similarity between two square (N×N) image "tiles" A and B-taken from corresponding (coordinate) positions of respective first and second images—according to the relationship:

$$F_{SSIM}(A, B) = \frac{(2\mu_A\mu_B + C_1)(2\sigma_{AB} + C_2)}{(\mu_A^2 + \mu_B^2 + C_1)(\sigma_A^2 + \sigma_B^2 + C_2)}$$

in which:
$\mu_A$ is the average of/over A;
$\mu_B$ is the average of/over B;
$\sigma_A^2$ is the variance in/of A;
$\sigma_B^2$ is the variance in/of B;
$\sigma_{AB}$ is the covariance of A and B;
$C_1 = k_1 L^2$ and $C_2 = k_2 L^2$ are "smoothing" variables that prevent "runaway" in the case of small denominator values, where:
L is the dynamic range of the pixel values in A and B; typically, $L = 2^n - 1$, where n is the number of bits per pixel;
$k_1$ and $k_2$ are set to conventional values of 0.01 and 0.03, respectively.

This value is typically calculated only for luma (not chrominance), and will yield a number (FOM) whose magnitude range depends on the employed normalization but is conventionally located between an upper-limit value of +1 (exact image match) and a lower-limit value of either −1 or 0 (total image mismatch).

On a related note, one can also define a "dissimilarity" SSIM (DSSIM), e.g. on the basis of a definition such as:

$$F_{DSSIM}(A, B) = \frac{1 - F_{SSIM}(A, B)}{N}$$

where N is a normalizing factor, e.g. N=2. Such a metric can also be used in the current invention, if so desired.

The current invention is not limited to the use of the abovementioned SSIM, and one can elect to use other ISMs, if desired. Other examples of ISMs include, for instance:

Mean Squared Error (MSE), which is defined as follows:

$$F_{MSE}(A, B) = \frac{1}{mn}\sum_{i=0}^{m-1}\sum_{j=0}^{n-1}[A(i, j) - B(i, j)]^2$$

for two m×n monochrome images A and B (or image portions at corresponding coordinates). This will conventionally yield a number (FOM) with a value that is dependent on the image pixel value normalization; for example:
For image pixel values in the range 0-1, $F_{MSE}$ will also lie in the range 0-1, with 0 corresponding to exact image match and 1 corresponding to total image mismatch;
For image pixel values in the range 0-255, $F_{MSE}$ will lie in the range $0\text{-}255^2$, with 0 corresponding to exact image match and $255^2$ corresponding to total image mismatch.

Peak Signal-to-Noise Ratio (PSNR), which is defined as follows:

$$F_{PSNR} = 10\log_{10}\frac{P_{MAX}^2}{F_{MSE}}$$

where $F_{MSE}$ is as set forth in the previous item, and $P_{MAX}$ is the maximum possible pixel value in the images in question; for example:
$P_{MAX}$ has a value of 255 for pixels represented using 8 bits per sample;
$P_{MAX}$ has a more generic value of $2^N - 1$ for pixels represented using N bits per sample.
An advantage of PSNR is that its value is (ultimately) independent of the image pixel value range.

Mutual Information of Regions (MIR), which is defined as follows:

$$F_{MIR}(A, B) = \sum_{a \in A}\sum_{b \in B} p(a, b)\log\left(\frac{p(a, b)}{p(a)p(b)}\right)$$

where:
p(a, b) is the joint probability distribution function of A and B;
p(a), p(b) are the marginal probability distribution functions of A and B, respectively.
This can be normalized in such a way that, for example, it will yield a value of 0 for total image mismatch, and a value of 1 for exact image match.

More information on the mathematics of image comparison (as applied in other disciplines) can, for example, be gleaned from the publication by A. A. Goshtasby, Image registration, Advances in Computer Vision and Pattern Recognition, Chapter 2, Springer-Verlag, London (2012) [DOI 10.1007/ 978-1-4471-2458-0_2]. It should be explicitly noted that mathematical ISMs as used in the present invention are of an intrinsically different nature to, for example, emission yield measures and other such scalarizing measures; for instance, if a feature of a fixed area changes position and/or shape within an image field, then a mathematical ISM will register this change, whereas a scalarizing measure will not. More specifically:

The mathematical ISM of the present invention compares two distributions on a member-by-member basis, and distills a metric value from that comparison (multivariate approach);

A scalarizing measure first converts each distribution into a number (thereby destroying certain specifics of each distribution), and then compares the two numbers in question.

Scalarizing measures are often used for end-point detection in etching, whereby a marked brightness change (e.g. corresponding to cumulative secondary electron yield) coincides with (complete) removal of a given (e.g. relatively high-brightness) material from an underlying (e.g. relatively low-brightness) substrate; to this end, a relatively bright marker material (such as gold) may be deliberately introduced to a given depth in a specimen, to act as an imaging "beacon" that will quench (and thus influence the integrated yield) when it is etched away.

As set forth above, if a non-acceptable FOM value is obtained in aforementioned cases (a) or (c), then one can repeat the surface modification procedure in the hope of obtaining a better FOM value. This can be done "blindly" (in a "hit-and miss" manner); however, in a particular embodiment of the present invention, it is instead done "intelligently" (in a "steered" manner). In this latter case, the primary figure of merit (arising from the primary modification step) is used to adjust at least one parameter of a secondary modification step, performed on the (newly created) second surface. In other words, the primary FOM (or some derivative/hybrid thereof) is used as input to a feedback loop in which one or more parameters of the surface modification procedure are (continually) fine-tuned so as to speed up convergence to an acceptable final FOM value. Examples of such parameters are, for example:

The thickness-setting for a mechanical cutting tool;

The beam energy and/or scan speed (dwelling time per position) for a focused particle beam milling tool;

The etchant temperature/pressure/flow rate and/or etch time for a chemical etching tool;

The precursor gas pressure/flow rate and/or beam energy/ scan-speed for a beam-induced deposition tool;

The deposition speed (e.g. sputter rate or evaporation temperature) and/or deposition time for a PVD tool;

The precursor gas pressure/flow rate and/or deposition time for a CVD tool.

If it is known (or suspected) that a particular parameter linearly influences the thickness of material removed from/ added to a surface, then such adjustment might (for example) be (partially) governed by a relationship of the following form:

$$\text{Parameter\_new} = \text{Parameter\_old} \times (1 - \text{FOM\_present}/\text{FOM\_ideal})$$

or a hybrid/derivative hereof.

In another (somewhat related) embodiment of the invention, said primary figure of merit is used to quantify a thickness change produced in said specimen by said primary modification step. This can, for example be done on the basis of one or more of:

Prior calibration(s);

A physical model of how the FOM varies as a function of thickness change;

Extrapolation/interpolation on the basis of previously obtained data pairs, etc. Quantifying the (subtractive or additive) thickness change in this way allows a more exact assessment of the nature/extent of further thickness change required, as well as allowing correction/fine tuning of the surface modification process itself.

The invention will now be elucidated in more detail on the basis of exemplary embodiments and the accompanying schematic drawings, in which:

FIG. 1 renders a longitudinal cross-sectional elevation of a particular type of CPM in which an embodiment of the current invention can be carried out.

FIG. 2A graphically depicts an ISM FOM value—calculated according to the invention—for multiple iterations of a surface modification technique performed on a mouse brain specimen.

Figure 2A:
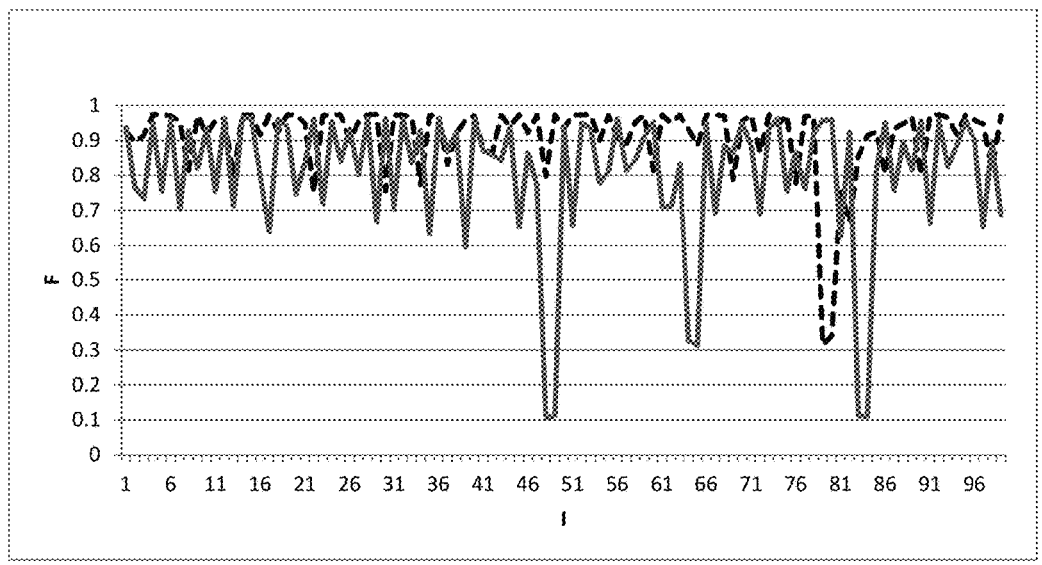
FIG. 2B shows a nominal image of an exposed surface of the mouse brain specimen used in generating FIG. 2A.
Figure 4A:
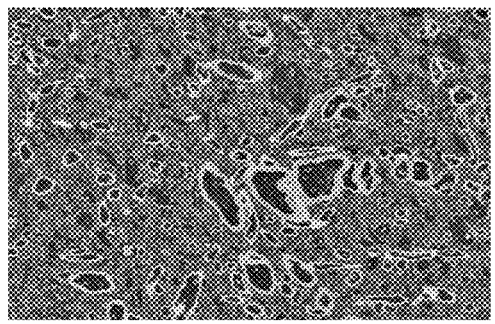
Figure 4B:
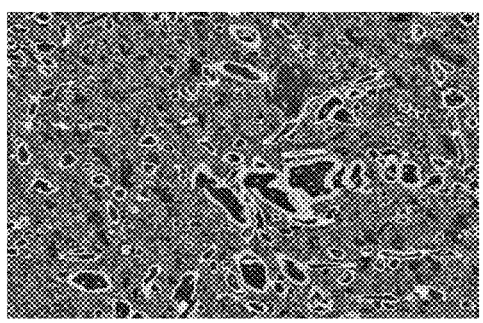
Figure 4C:
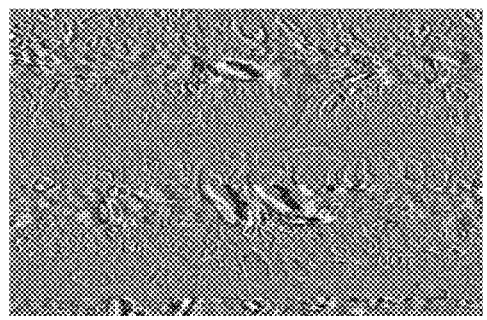

FIGS. 4A-4C reveal an acquisition error associated with one of the surface modification iterations of FIG. 2A, resulting in a flagged FOM value.

Figure 5A:
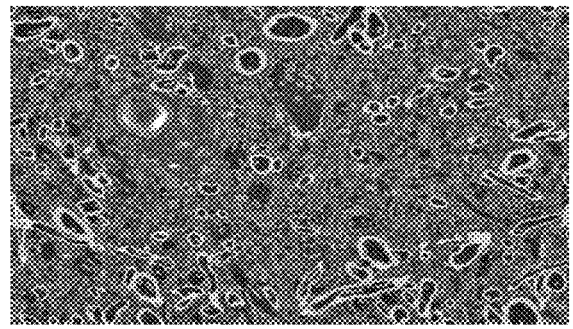
Figure 5B:
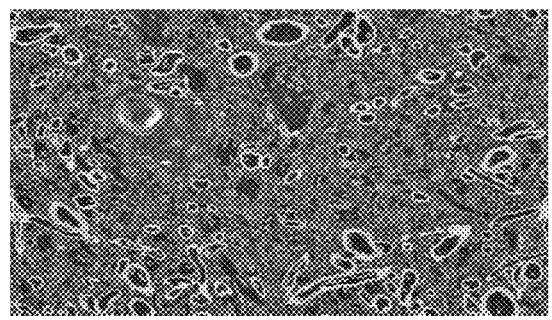
Figure 5C:
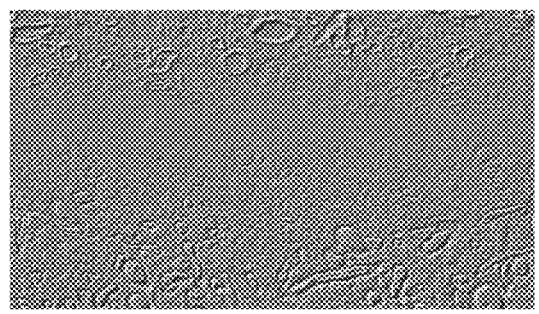

FIGS. 5A-5C reveal an imaging error associated with one of the surface modification iterations of FIG. 2A, resulting in a flagged FOM value.

EMBODIMENT 1

Figure 1:
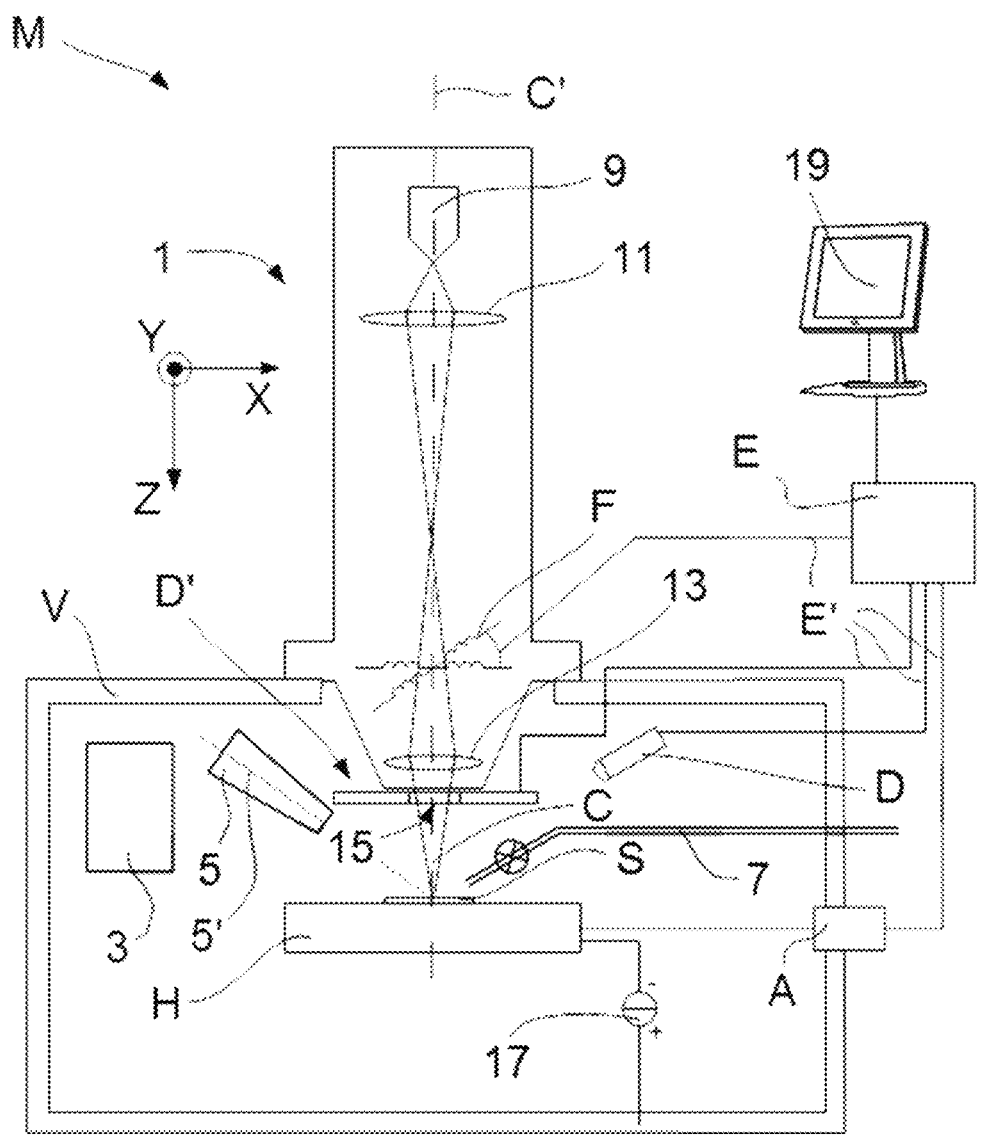

FIG. 1 is a highly schematic depiction of an embodiment of a CPM that lends itself to use in conjunction with the present invention; more specifically, it shows an embodiment of a scanning-type microscope M, which, in this case, is a SEM (though, in the context of the current invention, it could just as validly be an ion-based microscope, for example, or a TEM, for instance). The microscope M comprises a particle-optical column/illuminator 1, which produces a beam C of input charged particles (in this case, an electron beam) that propagates along a particle-optical axis C'. The particle-optical column 1 is mounted on a vacuum chamber V, which comprises a specimen holder H and associated stage/actuator A for holding/positioning a specimen S. The vacuum chamber V is evacuated using vacuum pumps (not depicted). With the aid of voltage source 17, the specimen holder H, or at least the specimen S, may, if desired, be biased (floated) to an electrical potential with respect to ground.

The particle-optical column 1 comprises an electron source 9 (such as a Schottky emitter), (electrostatic/magnetic) lenses 11, 13 (in general, more complex in structure than the schematic depiction here) to focus the electron beam C onto the specimen S, and a deflection unit F to perform beam deflection/scanning of the beam C. When the beam C impinges on/is scanned across the specimen S, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, D, D', which may, for example, be embodied as follows:

Detector D may, for example, be an electron detector (such as an SSPM), X-ray detector (such as an SDD or Si(Li) sensor) or a light detector (such as a photodiode).

Detector D' is a segmented electron detector, comprising a plurality of independent detection segments (e.g. quadrants) disposed about a central aperture 15 (allowing passage of the beam C). Such a detector can, for example, be used to investigate (the angular dependence of) a flux of output (secondary or backscattered) electrons emerging from the specimen S.

These are just examples, and the skilled artisan will understand that other detector types, numbers and geometries/configurations are possible.

The microscope M further comprises a controller/computer processing unit E for controlling inter alia the deflection unit F, lenses 11 and 13, and detectors D, D', and displaying information gathered from the detectors D, D' on a display unit 19 (such as a flat panel display); such control occurs via control lines (buses) E'. The controller E (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

In the context of the current invention, the microscope M also comprises in situ surface modification apparatus, which can be invoked to modify a presented (top) surface of the specimen S by performing thereon a process such as material removal, material deposition, etc. As already indicated above, such apparatus can take many different forms, and only a few possibilities (out of many) are shown in the present Figure. More particularly:

Item 3 is, for example, an in situ mechanical cutting tool, such as a (retractable) microtome, knife or mill. Alternatively, it might be an in situ deposition station, e.g. for performing PVD or CVD, or an etching unit. When desired, the specimen holder H can be moved by actuator A so as to "visit" item 3 for performance of controlled surface modification on specimen S.

Item 5 is a secondary particle-optical column, which in the current case is an ion column, for example. It has an associated secondary particle-optical axis 5', which typically intersects axis C' within a plane of specimen S. It can, for example, be used to perform ion milling on specimen S. Alternatively, in combination with gas admission conduit 7 (which can be used to admit a controllable flow of a particular precursor gas), it can be used to perform IBID or IBIE. One could also, of course, reverse the roles/natures of items 1 and 5, using an ion column for imaging and an electron column for performing EBID or EBIE, for example.

In practice, only one of items 3, 5 might be present. Alternatively, there might be even more of such surface modification modules present. Moreover, as set forth above, use could also be made of one or more ex situ surface modification devices/tools, located outside the chamber/enclosure V. Such considerations are matters of choice, available space, desired versatility, etc.

When surface modification is performed on specimen S (e.g. using item 3 and/or 5), its ultimate goal will be to remove or add a desired layer thickness from/to an initial surface of the specimen S. In practice, however, it may fail to (satisfactorily) achieve this purpose, and instead remove/add too little or too much material, and/or damage/corrupt the specimen surface, e.g. by producing debris/contamination thereon. In certain instances, such situations will—to some (limited) extent—qualitatively manifest themselves when the specimen S is returned to its inspection position under particle-column 1, allowing the newly produced specimen surface to be imaged (and visually inspected by a microscope operator) or otherwise studied (e.g. via a spectrum and/or diffractogram). However, a quantitative inspection routine would be much more valuable—particularly one that could be performed (semi-)automatically. The current invention provides such quantitative information, in that it uses (autonomous) mathematical comparison of "before" and "after" imagery to produce a meaningful numerical "score" or "grade" (FOM) for the surface modification step last performed on the specimen. As explained above, this score value can then be used to (autonomously) make a decision as to whether or not said surface modification was acceptable and—if it wasn't—can be used as a basis to (autonomously) perform/tailor follow-on surface modification iterations. Such calculations, analysis and control can be performed by (software/firmware running in) processor E or another (dedicated) processor unit.

EMBODIMENT 2

FIG. 2A graphically depicts an ISM FOM value—calculated according to the present invention—for multiple iterations of a surface modification technique performed on a mouse brain specimen. In this particular case, a microtome was used to repeatedly shave a given film thickness $d_S$ off of the specimen, whereby:

In one set of iterations, $d_S$=10 nm (dashed line in FIG. 2A);

In another set of iterations, $d_S$=20 nm (solid line in FIG. 2A).

An image of the freshly modified surface of the specimen was taken after each iteration and, according to the invention, an ISM FOM value was calculated for each corresponding pair of "before" and "after" images pertaining to each iteration (the "before" image being the image taken after the preceding iteration). More particularly, in the current case, each image was divided into 2048×2048 "pixels" or "tiles" and $F_{SSIM}(A, B)$ was calculated according to the formula given above. This value (F) was then plotted against iteration index (I) to yield FIG. 2A, whereby the vertical axis (F value) is subdivided into ten "decades" or "bands", each with a height/extent of 0.1. From an inspection of FIG. 2A, the following is evident:

For 10 nm cuts (dashed line), the F value is very often in the uppermost band (0.9-1), and only relatively occasionally outside it (a notable exception (spike) being at index 80, which will be discussed in more detail below with respect to FIGS. 4A-4C). This indicates that, in many cases, the surface modification is failing to remove material from the specimen (F equal, or very close, to 1).

Figure 3A:
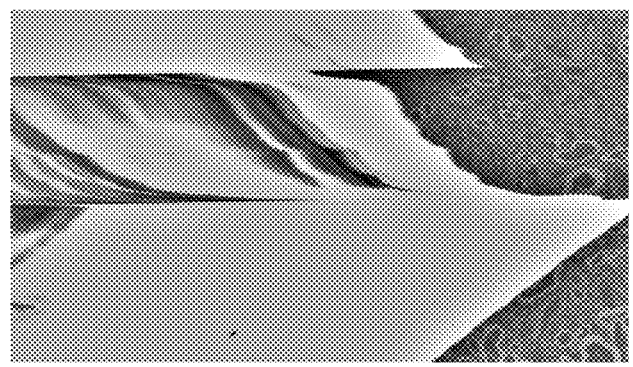
FIGS. 3A and 3B show images of situations in which one of the surface modification iterations of FIG. 2A caused corruption/contamination of the specimen surface, resulting in an out-of-spec FOM value.
Figure 3B:
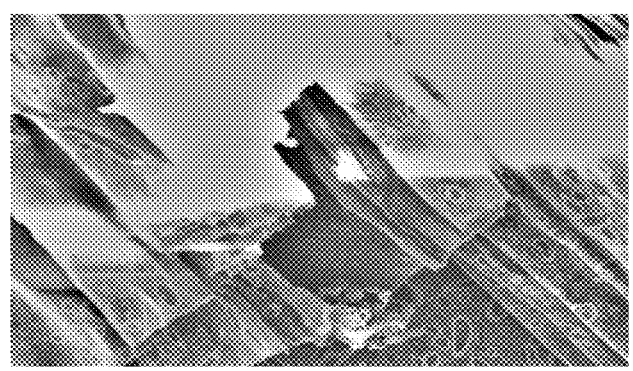

For 20 nm cuts (solid line), there are still some data points in the uppermost band (0.9-1), but most are now in a "nominal" band such as 0.6-0.7/0.7-0.8. Notable exceptions (spikes) occur at the following indices:

48 and 83, which will be discussed in more detail below with respect to FIGS. 3A, 3B;

64, which will be discussed in more detail below with respect to FIGS. 5A-5C. According to the invention, noticeable spikes into/toward the lower bands of FIG. 2A (F values relatively close to 0) can be construed as indicators that a surface modification iteration has not proceeded according to plan, as will now be elucidated in greater detail.

Figure 2B:
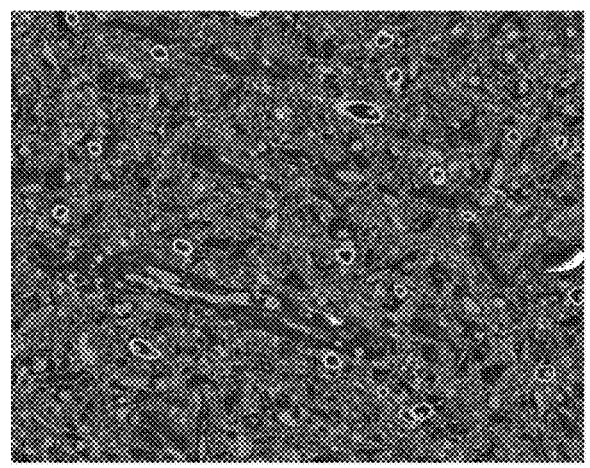

FIG. 2B shows a nominal image of an exposed surface of the mouse brain specimen used in generating FIG. 2A; this is an example of how the specimen is "supposed to" look after a satisfactorily executed surface modification iteration, and it will be used as a reference/standard for the discussion below.

Turning back to FIG. 2A, this shows two deep spikes onto the boundary of the lowermost F-value band (0-0.1), namely one at index 48 and one at index 83 (both of which occur in the measurement set with $d_S$=20 nm). According to the invention, such low F-values (proximal to zero) can be interpreted as an indicator that a surface modification iteration has corrupted the surface of the specimen, and this interpretation is corroborated by FIGS. 3A and 3B, which show post-surface-modification specimen images respectively corresponding to these two indices (I 48 in FIG. 3A; 183 in FIG. 3B). These Figures clearly show the presence of debris on the specimen surface—most likely in the form of a thin flake of specimen that has fallen onto the freshly exposed surface after a thinning step.

Also present in FIG. 2A are two spikes that extend as far as the boundary of the third-lowest F-value band (0.2-0.3)—one occurring around I 64 ($d_S$=20 nm) and the other occurring around I 80 ($d_S$=10 nm).

Starting with the second of these, FIGS. 4A and 4B show specimen images at indices I 79 and I 80, respectively, and FIG. 4C shows a "difference image" obtained by subtracting one image from the other. Careful inspection of FIG. 4B reveals a discontinuity in the form of a sudden intra-image lateral shift (about ⅔ of the way up from the bottom of the image)—probably caused by a sudden jump in beam/stage scan position during image acquisition. The difference image in FIG. 4C reveals this shift more clearly, together with two other such shifts—which seem to occur (quasi-)periodically (from bottom to top of the image). As a result of these shifts, the F-value is significantly reduced (F-0.3). Such F-value behavior can be interpreted as a flag that there is a problem (in this case, a scanning error), and that a system check might be a worthwhile undertaking.

FIGS. 5A and 5B show specimen images at indices I 63 and I 64, respectively, and FIG. 5C shows a "difference image" obtained by subtracting one image from the other. Careful inspection of FIG. 5B (by a trained eye) indicates the presence of image distortion (probably caused by lens aberrations), principally near the upper and lower edges. The difference image in FIG. 5C reveals this distortion more clearly, with a relatively featureless "plain" across the middle of the image, but with pronounced "topography" along its upper and lower edges. As a result of this distortion, the F-value is significantly reduced (F-0.3). Once again, such F-value behavior can be interpreted as a flag that there is a problem (in this case, an aberration issue), and that a system check would be prudent.

The invention claimed is:

1. A method of investigating a specimen using a charged-particle microscope comprising:
   a specimen holder, for holding the specimen;
   a source, for producing a beam of charged-particle radiation;
   an illuminator, for directing said beam so as to irradiate a surface of the specimen;
   an imaging detector, for receiving a flux of radiation emanating from the specimen in response to said irradiation, so as to produce an image of at least part of said surface; and
   an apparatus for modifying said surface by performing thereon a process selected from the group consisting of material removal, material deposition, and combinations thereof, wherein the apparatus has a set of operating parameters;
   the method comprising:
   defining a lower threshold and an upper threshold for comparison with a primary figure of merit;
   producing and storing a first image, of a first, initial surface of the specimen;
   setting the operating parameters for the apparatus;
   modifying said first surface in a primary modification step by invoking said apparatus, thereby yielding a second, modified surface;
   producing and storing a second image, of said second surface;
   performing a pixel-wise comparison of said first and second images using a mathematical image similarity metric so as to generate the primary figure of merit for said primary modification step, wherein the primary figure of merit quantifies the similarity of the first and second images, and wherein a changing primary figure of merit indicates a changing similarity of the first and second images; and
   comparing the primary figure of merit to the lower and upper thresholds, wherein if the primary figure of merit is above the upper threshold indicating a first outcome of the primary modification step as indicated by the similarity of the first and second images, performing a first surface modification operation, and wherein if the primary figure of merit is below the lower threshold indicating an outcome of the primary modification step different from the first outcome as indicated by the similarity of the first and second images, performing a second surface modification operation, different from the first surface modification operation.

2. The method according to claim 1, wherein said primary figure of merit is used to adjudge at least one of the following scenarios:
   said primary modification step failed to modify said first surface;
   said primary modification step insufficiently modified said first surface; and
   said second surface is corrupted relative to said first surface.

3. The method according to claim 1, wherein, in a subsequent iteration, said primary figure of merit is used to adjust at least one parameter of a secondary modification step, performed on said second surface.

4. The method according to claim 1, wherein said primary figure of merit is used to quantify a thickness change produced in said specimen by said primary modification step.

5. The method according to claim 1, wherein said image similarity metric is selected from the group consisting of SSIM, MSE, PSNR, MIR, hybrids thereof, and combinations thereof.

6. The method according to claim 1, wherein said apparatus is selected from the group consisting of a mechanical cutting tool, a focused particle beam milling tool, an etching apparatus, a beam-induced deposition tool, a physical vapor deposition apparatus, a chemical vapor deposition apparatus, and combinations thereof.

7. The method according to claim 1, wherein said apparatus is located in situ in said charged-particle microscope.

8. A charged-particle microscope comprising:
a specimen holder, for holding a specimen, wherein the specimen has a surface to be processed;
a source, for producing a beam of charged-particle radiation;
an illuminator, for directing said beam so as to irradiate the surface of the specimen; an imaging detector, for receiving a flux of radiation emanating from the specimen in response to said irradiation, so as to produce an image of at least part of said surface;
an apparatus for modifying the surface by performing thereon a process selected from the group consisting of material removal, material deposition, and combinations thereof, wherein the apparatus has a set of operating parameters; and
an electronic processor that is programmed to:
control, and adjust the operating parameters of, the apparatus;
acquire a first image from the specimen;
modify the surface of the specimen in a primary modification step using the apparatus and then acquire a second image from the specimen;
use a mathematical image similarity metric to perform pixel-wise comparison of first and second images to generate a numerical figure of merit that quantifies the similarity of the first and second images, wherein a change in value of the numerical figure of merit would indicate a change in similarity of the first and second images;
compare the numerical figure of merit to an upper threshold and perform a first surface modification operation if the numerical figure of merit is above the upper threshold indicating a first outcome of the primary modification step as indicated by the similarity of the first and second images; and
compare the numerical figure of merit to a lower threshold and, if the numerical figure of merit is below the lower threshold indicating an outcome of the primary modification step different from the first outcome as indicated by the similarity of the first and second images, perform a second surface modification operation, different from the first surface modification operation.

9. The charged particle microscope according to claim 8, wherein said processor is programmed to;
compile said first image prior to said primary modification step;
compile said second image after the primary modification step; and
use said numerical figure of merit to assign a success rating to the primary modification step.

10. The charged particle microscope of claim 9, wherein said numerical figure of merit is selected from the group consisting of SSIM, MSE, PSNR, MIR, hybrids thereof, and combinations thereof.

11. The charged particle microscope of claim 10, wherein said numerical figure of merit is used to quantify a thickness change produced in said specimen by said primary modification step.

12. The method according to claim 2, wherein, in a subsequent iteration, said primary figure of merit is used to adjust at least one parameter of a secondary modification step, performed on said second surface.

13. The method according to claim 12, wherein said primary figure of merit is used to quantify a thickness change produced in said specimen by said primary modification step.

14. The method according to claim 2, wherein said primary figure of merit is used to quantify a thickness change produced in said specimen by said primary modification step.

15. The method according to claim 2, wherein said apparatus is selected from the group consisting of a mechanical cutting tool, a focused particle beam milling tool, an etching apparatus, a beam-induced deposition tool, a physical vapor deposition apparatus, a chemical vapor deposition apparatus, and combinations thereof.

16. The method according to claim 1, further comprising repeating the modifying the surface of the specimen using the apparatus, the using a mathematical image similarity metric, and the comparing the primary figure of merit to a lower threshold and to an upper threshold.

17. The method according to claim 1, wherein in the performing a pixel-wise comparison of said first and second images using a mathematical image similarity metric so as to generate the primary figure of merit for said primary modification step, an increasing primary figure of merit indicates an increasing similarity of the first and second images.

18. The method according to claim 17, wherein in the comparing the primary figure of merit to the lower and upper thresholds, the first operation comprises repeating the setting the operating parameters for the apparatus, and the second operation comprises cleaning or reconditioning the surface of the specimen.

19. The charged particle microscope according to claim 8, wherein in the use of a mathematical image similarity metric to perform pixel-wise comparison of first and second images to generate a numerical figure of merit, an increasing numerical figure of merit indicates an increasing similarity of the first and second images.

20. The charged particle microscope according to claim 19, wherein in the comparison of the numerical figure of merit to a lower threshold and to an upper threshold, the first operation comprises repeating the setting the operating parameters for the apparatus, and the second operation comprises cleaning or reconditioning the surface of the specimen.

* * * * *